(12) United States Patent
Dai et al.

(10) Patent No.: US 7,820,834 B2
(45) Date of Patent: Oct. 26, 2010

(54) TRIPTOLIDE 5,6-DERIVATIVES AS IMMUNOMODULATORS AND ANTICANCER AGENTS

(75) Inventors: Dongcheng Dai, Mountain View, CA (US); John H. Musser, San Carlos, CA (US); Hongwei Yuan, Burlingame, CA (US)

(73) Assignee: Pharmagenesis, Inc., Redwood City, CA (US)

( * ) Notice: Subject to any disclaimer, the term of this patent is extended or adjusted under 35 U.S.C. 154(b) by 705 days.

(21) Appl. No.: 10/584,114

(22) PCT Filed: Dec. 20, 2004

(86) PCT No.: PCT/US2004/043249

§ 371 (c)(1),
(2), (4) Date: May 21, 2007

(87) PCT Pub. No.: WO2005/062913

PCT Pub. Date: Jul. 14, 2005

(65) Prior Publication Data

US 2007/0249048 A1    Oct. 25, 2007

(51) Int. Cl.
C07D 493/22    (2006.01)
(52) U.S. Cl. .................................................. 549/297
(58) Field of Classification Search ................ 549/297; 514/453
See application file for complete search history.

(56) References Cited

U.S. PATENT DOCUMENTS

| | | | |
|---|---|---|---|
| 4,005,108 A | 1/1977 | Kupchan et al. |
| 5,192,817 A | 3/1993 | Takaishi et al. |
| 5,294,443 A | 3/1994 | Lipsky et al. |
| 5,430,054 A | 7/1995 | Qian et al. |
| 5,468,772 A | 11/1995 | Xu et al. |
| 5,580,562 A | 12/1996 | Lipsky et al. |
| 5,648,376 A | 7/1997 | Strobel et al. |
| 5,663,335 A | 9/1997 | Qi et al. |
| 5,759,550 A | 6/1998 | Weidmann et al. |
| 5,843,452 A | 12/1998 | Weidmann et al. |
| 5,919,816 A | 7/1999 | Hausheer et al. |
| 5,962,516 A | 10/1999 | Qi et al. |
| 5,972,998 A | 10/1999 | Jung et al. |
| 6,004,999 A | 12/1999 | Jung et al. |
| 6,011,042 A | 1/2000 | Greenwald et al. |
| 6,103,875 A | 8/2000 | Martinez-Miller et al. |
| 6,150,539 A | 11/2000 | Musser |
| 6,294,546 B1 | 9/2001 | Rosen et al. |
| 6,329,148 B1 | 12/2001 | Rosen et al. |
| 6,458,537 B1 | 10/2002 | Staub et al. |
| 6,537,984 B2 | 3/2003 | Rosen et al. |
| 6,548,537 B1 | 4/2003 | Dai et al. |
| 6,569,893 B2 | 5/2003 | Dai et al. |
| 6,599,499 B1 | 7/2003 | Rosen et al. |
| 6,620,843 B2 | 9/2003 | Fidler et al. |
| 6,777,441 B2 | 8/2004 | Wang et al. |
| 6,943,259 B2 | 9/2005 | Dai et al. |
| 7,019,151 B2 | 3/2006 | Dai et al. |
| 7,098,348 B2 | 8/2006 | Dai et al. |
| 7,417,069 B2 | 8/2008 | Dai et al. |
| 7,626,044 B2 * | 12/2009 | Li et al. ...................... 549/297 |
| 2002/0077350 A1 | 6/2002 | Babish et al. |
| 2002/0099051 A1 | 7/2002 | Fidler et al. |
| 2004/0018260 A1 | 1/2004 | Ren et al. |
| 2004/0152767 A1 | 8/2004 | Dai et al. |
| 2004/0198808 A1 | 10/2004 | Dai et al. |
| 2004/0235943 A1 | 11/2004 | Dai et al. |
| 2005/0288645 A1 | 12/2005 | LaVon |
| 2007/0244080 A1 | 10/2007 | Fidler et al. |
| 2007/0249048 A1 | 10/2007 | Dai et al. |
| 2007/0282114 A1 | 12/2007 | An et al. |
| 2008/0287530 A1 | 11/2008 | Yuan et al. |

FOREIGN PATENT DOCUMENTS

| | | |
|---|---|---|
| CN | 1052859 A | 7/1991 |
| CN | 1317248 A | 10/2001 |
| EP | 0 156 643 B1 | 10/1985 |
| JP | 03 178977 | 8/1991 |
| WO | WO 94/26265 A1 | 11/1994 |
| WO | WO 98/52933 A1 | 11/1998 |
| WO | WO 98/52951 A1 | 11/1998 |

(Continued)

OTHER PUBLICATIONS

Anderson, Wayne K. et al., "Synthesis, Evaluation of Chemical Reactivity, and Murine Antineoplastic Activity of 2-Hydroxy-5-(3,4-dichlorophenyl)-6,7-bis(hydroxymethyl)-2,3-dihydro-1H-pyrrolizine Bis(2-propylcarbamate) and 2-Acyloxy Derivatives as Potential Water-Soluble Prodrugs[1]", *J. Med. Chem.*, 26:1333-1338 (1983).

(Continued)

*Primary Examiner*—Bernard Dentz
(74) *Attorney, Agent, or Firm*—King & Spalding LLP; Peter J. Dehlinger; Susan J. Myers Fitch

(57) ABSTRACT

Compounds useful as immunosuppressive, anti-inflammatory and anticancer agents and methods of their preparation and use are described. The compounds are analogs or derivatives of triptolide and related compounds, modified at the 5- and/or 6-position relative to the naturally occurring compounds.

5 Claims, 4 Drawing Sheets

FOREIGN PATENT DOCUMENTS

| | | |
|---|---|---|
| WO | WO 00/12483 A1 | 3/2000 |
| WO | WO 00/63212 | 10/2000 |
| WO | WO 02/070472 A1 | 9/2002 |
| WO | WO 02/074759 A1 | 9/2002 |
| WO | WO 03/101951 A2 | 12/2003 |
| WO | WO2004/058770 | 7/2004 |
| WO | WO2005/000291 | 1/2005 |
| WO | WO2005/020887 | 3/2005 |
| WO | WO 2005/062913 A2 | 7/2005 |
| WO | WO 2005/084365 A2 | 9/2005 |
| WO | WO 2006/012204 A2 | 2/2006 |

OTHER PUBLICATIONS

Aumuller, G. et al., "Intermediate filaments in sertoli cells", *Microscopy Research and Technique*, 20:50-72(1992).

Becker, K. et al., "Thioredoxin reductase as a pathophysiological factor and drug target", *Eur. J. Biochem.*, 267(20):6118-6125 (2000).

Berg, D. et al., "14-3-3 Proteins in the nervous system", *Nature Reviews Neuroscience*,. 4:752-62 (2003).

Britton, R. et al., "New okadaic acid analogues from the marine sponge *Merriamum oxeato* and their effect on mitosis", *J. Nat. Prod.*, 66:838-43 (2003).

Chang, W-T. et al., "Triptolide and chemotherapy cooperate in tumor cell apoptosis. A role for the p53 pathway", *The Journal of Biological Chemistry*, 276(3):2221-2227 (2001).

Chen et al., "Mechanisms of tolerance induced by PG490-88 in a bone marrow transplantation model", *Transplantation*, 73(1):115 (2002).

Chen et al., "Prevention of graft-versus-host disease by a novel immunosuppressant, PG490-88, through inhibition of alloreactive T cell expansion", *Transplantation*, 70(10):1442-1447 (2000).

Cheng et al., "Research on extraction technology of Tripterygium", *Chinese Journal of Pharmaceuticals*, 21(10):435-436 (No English translation) (1990).

Cheng, X.X. et al., Yao Xue Xue Bao, *ACTA Pharmaceutica Sinica*, 37:339-342 (2002) (English Abstract translation).

Dan et al. , "Studies on triepoxide analogs of triptolide", *Tetrahedron Letters*, 38(39):6865-6868 (1997).

De Groot Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin", *J. Med. Chem.*, 43:3093-3102 (2000).

De Quan Yu et al., "Chemical Transformation of Triptolide", *Chinese Chemical Letters*, 2(12):937-940 (1991).

Dittert, L.W. et al., "Acetaminophen Prodrugs I Synthesis, Physicochemical Properties, and Analgesic Activity", *Journal of Pharmaceutical Sciences*, 57(5):774-780 (1968).

Dittert, L.W. et al., "Acetaminophen Prodrugs II Effect of Structure and Enzyme Source on Enzymatic and Nonenzymatic Hydrolysis of Carbonate Esters", *Journal of Pharmaceutical Sciences*, 57(5):780-783 (1968).

Fidler, J.M. et al., "PG490-88, a derivative of triptolide, causes tumor regression and sensitizes tumors to chemotherapy", *Molecular Cancer Therapeutics*, 2(9):855-62 (2003).

Fidler, J.M. et al., "Immunosuppressive activity of the Chinese medicinal plant *Tripterygium wilfordii*. III. Suppression of graft-versus-host disease in murine allogeneic bone marrow transplantation by the PG27 extract", *Transplantation*, 74(4):445-457 (2002).

Fruman, D.A. et al., "Phosphoinositide Kinases", *Ann. Rev. Biochem.*, 67:481-507 (1998).

Fu et al., "14-3-3 Proteins: Structure, Function, and regulation", *Ann. Rev. Pharmacol. Toxicol.*, 40:617-47 (2000).

Gabbiani, G., "The myofibroblast in wound healing and fibrocontractive diseases", *Journal of Pathology*, 200:500-503 (2003).

Garcia, A. et al., "Serine/threonine protein phosphatases PP1 and PP2A are key players in apoptosis", *Biochimie*, 85:721-726 (2003).

Gilles, C. et al., "Transactivation of vimentin by beta-catenin in human breast cancer cells", *Cancer Research*, 63(10):2658-2664 (2003).

Gleichmann, E. et al., "Graft-versus-host reactions: clues to the etiopathology of a spectrum of immunological diseases", *Immunology Today*, 5(11):324-332 (1984).

Goto, Y. et al., "Augmented cytoplasmic Smad4 induces acceleration of TGF-beta1 signaling in renal tubulointerstitial cells of hereditary nephrotic ICGN mice with chronic renal fibrosis; possible role for myofibroblastic differentiation", *Cell Tissue Res.*, 315:209-221 (2004).

Gross, T.J. and Hunninghake, G.W., "Idiopathic pulmonary fibrosis", *N. Engl. J. Med.*, 345(7):517-525 (2001).

Hansen, Kristian T. et al., "Carbamate Ester Prodrus of Dopaminergic Compounds: Synthesis, Stability, and Bioconversion", *Journal of Pharmaceutical Sciences*, 80(8):793-798 (1991).

Hansen, Laila B. et al., "Ketobemidone prodrugs for buccal delivery", *Acta Pharm. Nord.*, 3(2):77-82 (1991).

He, Q. et al., "Neuroprotective eggects of *Tripterygium wilfordii* Hook F Monomer $T_{10}$ on glutamate induced PC12 cell line damage and its mechanism", *Beijing Da Xue Xue Bao, Journal of Peking University (Health Sciences)*, 35(3):252-5 (Jun. 2003) (English Abstract Translation).

Houtman, J.C. et al., "Early phosphorylation kinetics of proteins involved in proximal TCR-mediated signaling pathways", *Journal of Immunology*, 175(4):2449-2458 (2005).

Huang, Tien L. et al., "Hydrolysis of Carbonates, Thiocarbonates, Carbamates, and Carboxylic Esters of α-Naphthol, β-Naphthol, and ρ-Nitrophenol by Human, Rat, and Mouse Liver Carboxylesterases", *Pharmaceutical Research*, 10(5):639-648 (1993).

Jiang, X-H. et al., "Functional p53 is required for triptolide-induced apoptosis and AP-1 and nuclear factor-kappaB activation in gastric cancer cells",*Oncogene*, 20(55):8009-8018 (2001).

Jerums, G. et al., "Evolving concepts in advanced glycation, diabetic nephropathy, and diabetic vascular disease", *Archives of Biochemistry and Biophysics*, 419(1):55-62 (2003).

Jiarun, Z. et al., "Screening of active anti-inflammatory, immunosuppressive and antifertility components of *Tripterygium wilfordii*", ACTA Academiae Medicinae Sinicae 13(6):391-397 (English Abstract only) (1991).

Jones, S.L. et al. "A role for the actin-bundling protein L-plastin in the regulation of leukocyte integrin function", *Proc. Natl. Acad. Sci. USA*, 95(16):9331-9336 (1998).

Kahns, A. M. et al., "Prodrugs of Peptides. 18. Synthesis and Evaluation of Various Esters of Desmopressin (dDAVP)", *Pharmaceutical Research*, 10(1):68-74 (1993).

Kershenobich, D. et al., "Concise Review: Liver fibrosis and inflammation. A review", *Annals of. Hepatology*, 2(4):159-163 (2003).

Keyser, F. D. et al., "The role of T cells in Rheumatoid Arthritis", *Clinical Rgeumatology*, 14(Suppl 2):5-9 (1995).

Khanna, A.K. and Mehta, M.R., "Targeted in vitro and in vivo gene transfer into T lymphocytes: potential of direct inhibition of alloimmune activation", *BMC Immunology*, 7(26):1-10 (2006).

Korngold, B. and Sprent, J. "Lethal graft-versus-host disease after bone marrow transplantation across minor histocompatibility barriers in mice. Prevention by removing mature T cells from marrow", *J. Exp. Med.*, 148:1687-98 (1978).

Kurz, E.U. et al., "Modulation of human DNA topoisomerase IIalpha function by interaction with 14-3-3epsilon", *The Journal of Biological Chemistry*, 275(18):13948-13954 (2000).

Kutney, J.P. et al., "Studies with plant cell cultures of the Chinese herbal plant, *Tripterygium wilfordii*, Synthesis and biotransformation of diterpene analogues", *Heterocycles*, 44(1):2-11 (1997).

Larribere, L. et al., "PI3K mediates protection against TRAIL-induced apoptosis in primary human melanocytes", *Cell Death and Differentiation*, 11(10):1084-1091 (2004).

Leonard, C.T. et al., "PG490-88, a derivative of triptolide, attenuates obliterative airway disease in a mouse heterotopic tracheal allograft model", *Journal of Heart and Lung Transplantation*, 21(12):1314-1318 (2002).

Li, K.K. and Fidler, J.M., "PG490-88 erxerts 1-16 potent anticancer activity alone and in combination therapy in a nude mouse xenograft model", Proceedings of the American Association for Cancer Research Annual Meeting Mar. 2001, 42:73, Abstract #391 (2001).

Li, F-Q. et al., "Neurotrophic and neuroprotective effects of tripchlorolide, an extract of Chinese herb *Tripterygium wilfordii* Hook F, on dopaminergic neurons", *Experimental Neurology*, 179(1):28-37 (2003).

Li, F-Q. et al., "Triptolide, a Chinese herbal extract, protects dopaminergic neurons from inflammation-mediated damage through inhibition of microglial activation", *Journal of Neuroimmunology*, 148(1-2):24-31 (2004).

Lin, C.S. et al., "Upregulation of L-plastin gene by testosterone in breast and prostate cancer cells: identification of three cooperative androgen receptor-binding sequences", *DNA Cell Biology*, 19(1):1-7 (2000).

List, A.F. et al., "Vascular endothelial growth factor receptor-1 and receptor-2 initiate a phosphatidylinositide 3-kinase-dependent clonogenic response in acute myeloid leukemia cells.", *Experimental Hematology*, 32(6):526-535 (2004).

Lovell, M.A. et al. "Decreased thioredoxin and increased thioredoxin reductase levels in Alzheimer's disease brain", *Free Radical Biology & Medicine*, 28(3):418-27 (2000).

Lundstrom, J. et al., "A Pro to His mutation in active site of thioredoxin increases its disulfide-isomerase activity 10-fold. New refolding systems for reduced or randomly oxidized ribonuclease", *The Journal of Biological Chemistry*, 267(13):9047-9052 (1992).

Lundy, S.K. et al., "Cells of the synovium in rheumatoid arthritis", *Arthritis Research & Therapy*, 9(1):1-11 (2007).

Ma et al., "Isolation of 17-hydroxytriptolide and analogs as drugs", ACTA Pharmaceutica Sinica, 28(2):110-115 (1993). (English Abstract translation).

Mason et al., "Pharmacological therapy fir idiopathic pulmonary fibrosis", *Am. J. Respir. Crit. Care Med.*, 160:1771-1777 (1999).

Masters, S.C. and Fu, H., "14-3-3 Proteins mediate an essential anti-apoptotic signal", *The Journal of Biological Chemistry*, 276(48):45193-45200 (2001).

Matlin, S.A. et al., "Male antifertility compounds from *Tripterygium wilfordi Hook F.*", *Contraception*, 47:387-400 (1993).

Mesa, R.A. et al., "In vitro antiproliferative activity of the farnesyltransferase inhibitor R115777 in hematopoietic progenitors from patients with myelofibrosis with myeloid metaplasia", *Leukemia*, 17(5):849-55 (2003).

Gu, Ming et al., "Effect of Chinese herb *Tripterygium wilfordii* Hook F monomer triptolide on apoptosis of PC12 cells induced by Aβ1-42"*ACTA Physiologica Sinica*, 56(1):73-78 (2004) (English Abstract translation).

Murase, N. et al., "Hamster-to-rat heart and liver xenotransplantation with FK506 plus antiproliferative drugs", *Transplantation*, 55(4):701-708 (1993).

Nassar, M. N. et al., "Effects of Structural Variations on the Rates of Enzymatic and Nonenzymatic Hydrolysis of Carbonate and Carbamate Esters", *Journal of Pharmaceutical Sciences*, 81(3):295-298 (1992).

Ono, K. and Lindsey, E.S., "Improved technique of heart transplantation in rats", *Journal of Thoracic and Cardiovascular Surgery*, 57(2):225-29 (1969).

Ory, S. et al., "Protein phosphatase 2A positively regulates Ras signaling by dephosphorylating KSR1 and Raf-1 on critical 14-3-3 binding sites", *Current Biology*, 13(16):1356-1364 (2003).

Otsuka, M. et al., "Differential expression of the L-plastin gene in human colorectal cancer progression and metastasis", *Biochemical and Biophysical Research Communications*, 289(4):876-881 (2001).

Pei, J-J. et al. "Okadaic-acid-induced inhibition of protein phosphatase 2A produces activation of mitogen-activated protein kinases ERK1/2, MEK1/2, and p70 S6, similar to that in Alzheimer's disease", *American Journal of Pathology*, 163(3):845-858 (2003).

Powis, G. and Montfort, W.R., "Properties and biological activities of thioredoxins", *Ann.Rev. Pharmacol. Toxicol.*, 41:261-295 (2000).

Qiu, D. and Kao, P.N., "Immunosuppressive and anti-inflammatory mechanisms of triptolide, the principal active diterpenoid from the Chinese medicinal herb *Tripterygium wilfordii* Hook. f.", *Drugs R&D*, 4(1):1-18 (2003).

Qiu, D. et al., "Immunosuppressant PG490 (triptolide) inhibits T-cell interleukin-2 expression at the level of purine-box/nuclear factor of activated T-cells and NF-kappaB transcriptional activation", *The Journal of Biological Chemistry*, 274(19):13443-13450 (1999).

Redpath, N.T. et al., "Regulation of translation elongation factor-2 by insulin via a rapamycin-sensitive signalling pathway", *The EMBO Journal*, 15(9):2291-2297 (1996).

Reichert, T.E. et al., "Interleukin-2 expression in human carcinoma cell lines and its role in cell cycle progression", *Oncogene*, 19(4):514-525 (2000).

Sato, S. et al., "Modulation of Akt kinase activity by binding to Hsp90", *Proc Natl Acad Sci USA*, 97(20):10832-10837 (2000).

Savolainen, Jouko et al., "Synthesis and in vitroIn vivo evaluation of novel oral $N$-alkyl- and $N,N$-dialkyl-carbamate esters of entacapone", *Life Sciences*, 67:205-216 (2000).

Schlesinger, C. et al., "Constrictive (obliterative) bronchiolitis: diagnosis, etiology, and a critical review of the literature", *Annals of Diagnostics Pathology*,. 2(5):321-34 (1998).

Schlesinger, C. et al., "Constrictive (obliterative) bronchiolitis", *Current Opinion in Pulmonary Medicine*, 4:288-293 (1998).

Schwaller, M. et al., "Reduction-reoxidation cycles contribute to catalysis of disulfide isomerization by protein-disulfide isomerase", *The Journal of Biological Chemistry*, 278(9):7154-7159 (2003).

Selman, M. et al., "Idiopathic pulmonary fibrosis: prevailing and evolving hypotheses about its pathogenesis and implications for therapy", *Ann. Intern. Med.*, 134:136-151 (2001).

Shamon, L.A. et al., "Evaluation of the mutagenic, cytotoxic, and antitumor potential of triptolide, a highly oxygenated diterpene isolated from *Tripterygium wilfordii*", *Cancer Letters*, 112:113-117 (1997).

Shevchenko, A. et al., "Mass spectrometric sequencing of proteins silver-stained polyacrylamide gels", *Anal. Chem.*, 68(5):850-858 (1996).

Shevchenko, A. et al., "Linking genome and proteome by mass spectrometry: large-scale identification of yeast proteins from two dimensional gels", *Proc Natl Acad Sci USA*, 93:14440-14445 (1996).

Show, M. et al., "Reduced intratesticular testosterone concentration alters the polymerization state of the Sertoli cell intermediate filament cytoskeleton by degradation of vimentin", *Endocrinology*, 144(12):5530-6 (2003).

Solit, D. et al., "Hsp90 as a therapeutic target in prostate cancer", *Seminars in Oncology*, 30(5):709-16 (2003).

Sontag et al., "Protein phosphatase 2A is a critical regulator of protein kinase C zeta signaling targeted by SV40 small t to promote cell growth and NF-kappaB activation", *The EMBO Journal*, 16(18):5662-5671 (1997).

Stella, V.J. et al., "Prodrugs, Do they have advantages in Clinical Practice ?", *Drugs*, 29:455-473 (1985).

Tolstonog et al., "Role of the intermediate filament protein vimentin in delaying senescence and in the spontaneous immortalization of mouse embryo fibroblasts", *DNA and Cell Biology*, 20(9):509-29(2001).

Tunek, Anders et al., "Hydrolysis of $^3$H-Bambuterol, A Carbamate Prodrug of Terbutaline, in Blood from Humans and Laboratory Animals In Vitro", *Biochemical Pharmacology*, 37(20):3867-3876 (1988).

Van Tamelen et al., "Biogenetic-type total synthesis of (t, −) -triptonide and (.+ −.) -triptolide", STN International Database, CAPLUS database Document No. 96:143107 2 pages (1982).

Waller, D.G. and George, C.F., "Prodrugs", *Br. J. Clin. Pharmac.*, 28:497-507 (1989).

Wahlgren, C-F. et al, "Itch and inflammation induced by intradermally injected interleukin-2 in atopic dermatitis patients and healthy subjects", *Arch Dermatol Res.*, 287(6):572-580 (1995).

Wang, Z. et al., "Altered distribution of Sertoli cell vimentin and increased apoptosis in cryptorchid rats", *Journal of Pediatric Surgery*, 37(4):648-652 (2002).

Wang, J. et al., "Immunosuppressive activity of the Chinese medicinal plant *Tripterygium wilfordii*. I. Prolongation of rat cardiac and renal allograft survival by the PG27 extract and immunosuppressive synergy in combination therapy with cyclosporine", *Transplantation*, 70(3):447-455 (2000).

Wang, J. and Morris, R.E., "Effect of splenectomy and mono- or combination therapy with rapamycin, the morpholinoethyl ester of mycophenolic acid and deoxyspergualin on cardiac xenograft survival", *Transplantation Proceedings*, 23(1):699-702 (1991).

Wang, X. et al., "Mechanism of triptolide-induced apoptosis: Effect on caspase activation and Bid cleavage and essentiality of the hydroxyl group of triptolide", *J. Mol. Med.*, 84:405-415 (2006).

Weibel, Helle et al., "Macromolecular prodrugs IXX. Kinetics of hydrolysis of benzyl dextran carbonate ester conjugates in aqueous buffer solutions and human plasma", *Acta Pharm. Nord.*, 3(3):159-162 (1991).

Weng, G. et al. "Advances in studies on apoptosis induced by *Tripterygium wilfordii*", *Chinese Traditional and Herbal Drugs*, 33(11):1053-1054 (2002) (No English Abstract Translation).

Whitesell, L. et al., "The stress response: implications for the clinical development of hsp90 inhibitors", *Current Cancer Drug Targets*, 3(5):349-358 (2003).

Yamagishi, S. et al., "Advanced glycation end products inhibit de novo protein synthesis and induce TGF-beta overexpression in proximal tubular cells", *Kidney International*, 63(2):464-473 (2003).

Yamamoto, R. et al., "Pharmaceutical Studies on water-Soluble corticosteroid derivatives I. Stability of Hydrocortisone 21 Hemiesters in Solution", Journal of the Pharmaceutical Society of Japan, 46(8):855-862 (1971).

Yang, S. et al., "Triptolide Induces apoptotic death of T lymphocyte", *Immunopharmacology*, 40:139-149 (1998).

Yang, J. et al., "Disruption of the EF-2 kinase/Hsp90 protein complex: a possible mechanism to inhibit glioblastoma by geldanamycin", *Cancer Research*, 61(10):4010-4016 (2001).

Yang, S. et al., "Triptolide Inhibits the Growth and Metastasis of Solid Tumors", *Molecular Cancer Therapeutics*, 2:65-72 (2003).

Yano, H. et al., "Inhibition of histamine secretion by wortmannin through the blockade of phosphatidylinositol 3-kinase in RBL-2H3 cells", *The Journal of Biological Chemistry*, 268(34):25846-25856 (1993).

Yuan, G-H. et al., "Characterization of cells from pannus-like tissue over articular cartilage of advanced osteoarthritis", *OsteoArthritis and Cartilage*, 12(1):38-45 (2004).

Zhang et al., "Studies on Diterpenoids from leaves of *Tripterygium wilfordii*", ACTA Pharmaceutica Sinica, 28(2):110-115 (1993). (English Abstract translation).

Zheng et al., "Screening of active iantiinflammatory, immunosuppressive and antifertility components of *Tripterygium wilfordii*", Chemiacl Abstracts 117(9): Abstract No. 83085a (1992).

Zhou, H-F. et al., "Triptolide inhibits TNF-alpha, IL-1 beta and NO production in primary microglial cultures", *Neuroreport*, 14(7):1091-5 (2003).

Zhou, Y.X. et al., *Ai Zheng* 21:1108-8 (2002).

Englebienne et al., *Drug Design Reviews*, "The Place of Biosteric Sila Substitution in Drug Design", (2005).

Kupchan et al., J. Am. Chem. Soc., 94:7194-7195 (1972).

Leuenroth and Crews, Chemistry and Biology 12:1259-1268 (2005).

Ning et al., Tetrahedron, 59(23):4209-4213.

Shanmuganathan et al., *J. Med. Chem.*, 37:821-827 (1994).

Vierling et al., *Journal of Fluorine Chemistry*, 107:337-354 (2001).

Chen, J-Y et al., "Improved Preparation of Triptolide Extract", *Chinese Journal of Pharmaceutcials*, 20(5):195 and 200 (Dec. 31, 1989) (English translation of abstract and concise explanation of relevance from Foreign Office Action).

Textbook of Chinese Medicine Chemistry for Chinese Colleges of Traditional Chinese Medicine in the New Century (for Chinese Medicine Specialty), Kuang Hai-Xue p. 23, Chinese Press of Traditional Chinese Medicine (Jun. 30, 2003) (English translation of abstract and concise explanation of relevance from Foreign Office Action).

* cited by examiner

TRIPTOLIDE 5,6-DERIVATIVES AS IMMUNOMODULATORS AND ANTICANCER AGENTS

FIELD OF THE INVENTION

The present invention relates to compounds useful as immunosuppressive, anti-inflammatory and anticancer agents.

REFERENCES

Dai, D. et al., U.S. Pat. No. 6,569,893 (2003).
Fidler, J. M. et al., U.S. Pat. No. 6,620,843 (2003).
Gleichmann, E. et al., *Immunol. Today* 5:324 (1984).
Jung, M. J. et al., U.S. Pat. No. 5,972,998 (1999).
Jung, M. J. et al., U.S. Pat. No. 6,004,999 (1999).
He, Q. et al., *Beijing Da Xue Xue Bao* 35:252-5 (June 2003).
Krishna, G. et al., *Am. J. of Pathology* 158(3):997-1004 (March 2001).
Kupchan, S. M. et al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al., *J. Chin. Pharm. Sci.* 1:12 (1992).
Murase, N. et al., *Transplantation* 55:701 (1993).
Ning, L. et al., *Pure and Applied Chemistry* 75(2-3):389-392 (2003).
Ning, L. et al., *Tetrahedron* 59(23):4209-4213 (2003).
Ono and Lindsey, *J. Thor. Cardiovasc. Surg.* 57(2):225-29 (1969).
Panchagnula, R. and Thomas, N. S., *Intl J Pharmaceutics* 201(2):131-150 (2000).
Pu, L. et al., *Zhongguo Yaoli Xuebao* 11:76 (1990).
Qi, Y. et al., U.S. Pat. No. 5,663,335 (1997).
Qi, Y. et al., U.S. Pat. No. 5,962,516 (1999).
Qian, S. et al., U.S. Pat. No. 5,430,054 (1995).
Strobel, G. A. et al., U.S. Pat. No. 5,648,376 (1997).
Wang, J. and Morris, R. E., *Transplantation Proc.* 23:699 (1991).
Wang, X. et al., PCT Pubn. No. WO 2002/17931 (2002).
Wiedmann, T. et al., U.S. Pat. No. 5,843,452 (1998).
Zhou, Y. X. et al., *Ai Zheng* 21(10): 1108-8 (October 2002).

BACKGROUND OF THE INVENTION

Immunosuppressive agents are used in the treatment of autoimmune disease and in treating or preventing transplantation rejection, including graft-versus-host disease (GVHD). Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD), a condition in which transplanted marrow cells attack the recipient's cells. See, for example, U.S. Pat. Nos. 4,005,108, 5,294,443, 5,843,452, and 5,648,376, cited above.

Triptolide and certain of its derivatives have also been reported to show anticancer activity. See, for example, Kupchan et al., 1972, 1977, as well as co-owned U.S. Pat. No. 6,620,843, which is hereby incorporated by reference.

Triptolide derivatives often provide other benefits relative to native triptolide in areas such as formulation, pharmacokinetics and biodistribution, by virtue of differences in solubility and/or their activity as prodrugs. Such derivatives are described, for example, in Jung et al., U.S. Pat. Nos. 5,972,998 and 6,004,999, and Qian et al., U.S. Pat. No. 5,430,054, as well as co-owned U.S. Pat. No. 6,150,539 (Triptolide prodrugs having high aqueous solubility), U.S. Pat. No. 5,962,516 (Immunosuppressive compounds and methods), U.S. Pat. No. 5,663,335 (Immunosuppressive compounds and methods), and U.S. Pat. No. 6,569,893 (Amino acid derivatives of triptolide compounds as immune modulators and anticancer agents).

In general, these disclosures are directed to derivatives and/or prodrugs produced by synthetic modification of triptolides at the epoxy rings, hydroxyl groups, or the lactone ring. None of these earlier disclosures describe modifications at the 5 or 6 position of triptolide, as disclosed herein.

SUMMARY OF THE INVENTION

In one aspect, the invention provides compounds which are useful for immunosuppressive, anti-inflammatory and anticancer therapy. The compounds are represented, in one embodiment, by Formula I:

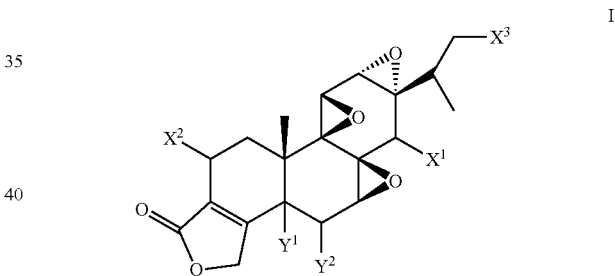

where $X^1$ is $OR^1$, where $R^1$ is selected from hydrogen, $C(=O)R^2$, and $C(=O)OR^2$, where $R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;

$X^2$ and $X^3$ are independently $OR^1$ or hydrogen, at least one of $X^2$ and $X^3$ being hydrogen; and where (i) $Y^1$ is hydrogen and $Y^2$ is selected from the group consisting of hydroxyl, halogen, cyano, nitromethyl, ethenyl ($-CH=CH_2$), $-CH_2COOR^4$, $N(R^4)_2$, and $SR^4$, where each $R^4$ is independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl, or, in the case of $N(R^4)_2$, taken together form a 5- to 7-member heterocyclic ring whose ring atoms are selected from the group consisting of carbon, nitrogen, oxygen and sulfur, wherein the ring atoms include at most 3 heteroatoms; or (ii) $Y^1$ is hydroxyl and $Y^2$ is selected from the group consisting of hydrogen, hydroxyl, halogen, cyano, $N(R^4)_2$, and $SR^4$; or (iii) $Y^1$ and $Y^2$ taken together form an epoxide ring.

The compounds are represented, in another embodiment, by Formula II:

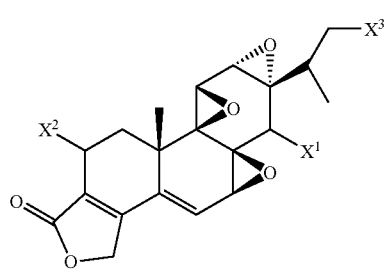

where $X^1$, $X^2$ and $X^3$ are as defined above.

Preferably, $X^1$ is selected from OH and OC(=O)$R^2$ (that is, $R^1$ is selected from hydrogen and C(=O)$R^2$). When $R^1$ is C(=O)$R^2$, $R^2$ is preferably selected from alkyl, aryl, aralkyl, and alkoxyalkyl, and is more preferably selected from alkyl, e.g. methyl or ethyl; aryl, e.g. phenyl, and aralkyl, e.g. benzyl. In one embodiment, $R^2$ is methyl.

When either of $X^2$ and $X^3$ is $OR^1$, preferred embodiments of $R^1$ are as described above.

In one embodiment, each of $X^2$ and $X^3$ is hydrogen.

One embodiment of the compounds of formula I is that in which (i) $Y^1$ is hydrogen and $Y^2$ is selected from the group consisting of hydroxyl, halogen, cyano, nitromethyl, ethenyl, —CH$_2$COOR$^4$, N(R$^4$)$_2$, and SR$^4$. Preferred embodiments of this class include those in which $Y^2$ is hydroxyl, fluoro, chloro, bromo, cyano, —CH$_2$COOR$^4$, or N(R$^4$)$_2$. In further preferred embodiments, $Y^2$ is hydroxyl, fluoro, chloro, bromo, or cyano. In one preferred embodiment, $Y^2$ is hydroxyl; in another preferred embodiment, $Y^2$ is cyano.

A further embodiment of the compounds of formula I is that in which (ii) $Y^1$ is hydroxyl and $Y^2$ is selected from the group consisting of hydrogen, hydroxyl, halogen, cyano, N(R$^4$)$_2$, and SR$^4$. Preferred embodiments of this class include those in which $Y^2$ is hydrogen, hydroxyl, fluoro, chloro, bromo, or cyano. In one embodiment, $Y^2$ is hydrogen; in a further embodiment, $Y^2$ is hydroxyl.

A further embodiment of the compounds of formula I is that in which (iii) $Y^1$ and $Y^2$ taken together form an epoxide ring.

The groups defined above as $R^2$, $R^3$, and $R^4$, when selected from alkyl, alkenyl, and alkynyl, preferably have up to six carbon atoms, more preferably up to four carbons, and, in selected embodiments, one or two carbons. When selected from cycloalkyl or cycloalkenyl, they preferably have 3 to 7, or, for cycloalkenyl, 5 to 7 carbon atoms. When selected from aralkyl, hydroxyalkyl, alkoxyalkyl, aryloxyalkyl, and acyloxyalkyl, the alkyl components of these groups preferably have up to six carbon atoms, more preferably up to four carbons, and, in selected embodiments, one or two carbons. In further selected embodiments, each of these groups is independently selected from alkyl, aryl, aralkyl, and alkoxyalkyl.

In other aspects, the invention provides a method of effecting immunosuppression, and a method of inducing apoptosis in a cell. The methods comprise administering to a subject in need of such treatment, or contacting said cell, respectively, with an effective amount of a compound of formula I or II as described above. The compound is typically provided in a pharmaceutically acceptable carrier. Specific embodiments of the methods may employ any of the specific embodiments of formula I or II described herein.

These and other objects and features of the invention will become more fully apparent when the following detailed description of the invention is read in conjunction with the accompanying drawings.

DETAILED DESCRIPTION OF THE INVENTION

I. Definitions

Figure 1:
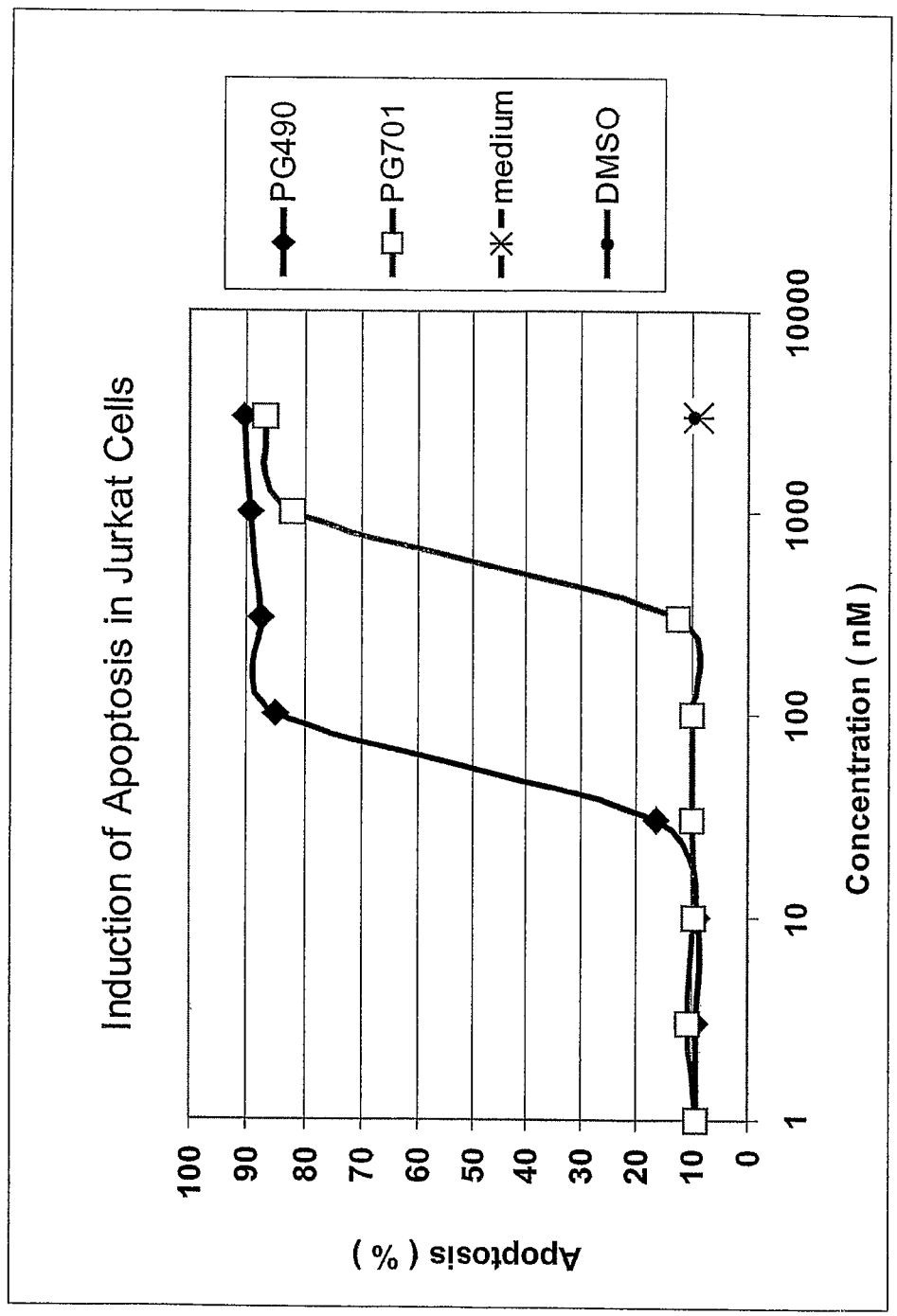
FIG. 1 shows dose-dependent induction of apoptosis in Jurkat cells by a compound of the invention, 5-α-hydroxy triptolide (designated PG701), in comparison with triptolide (designated PG490) (Example 8)
Figure 2:
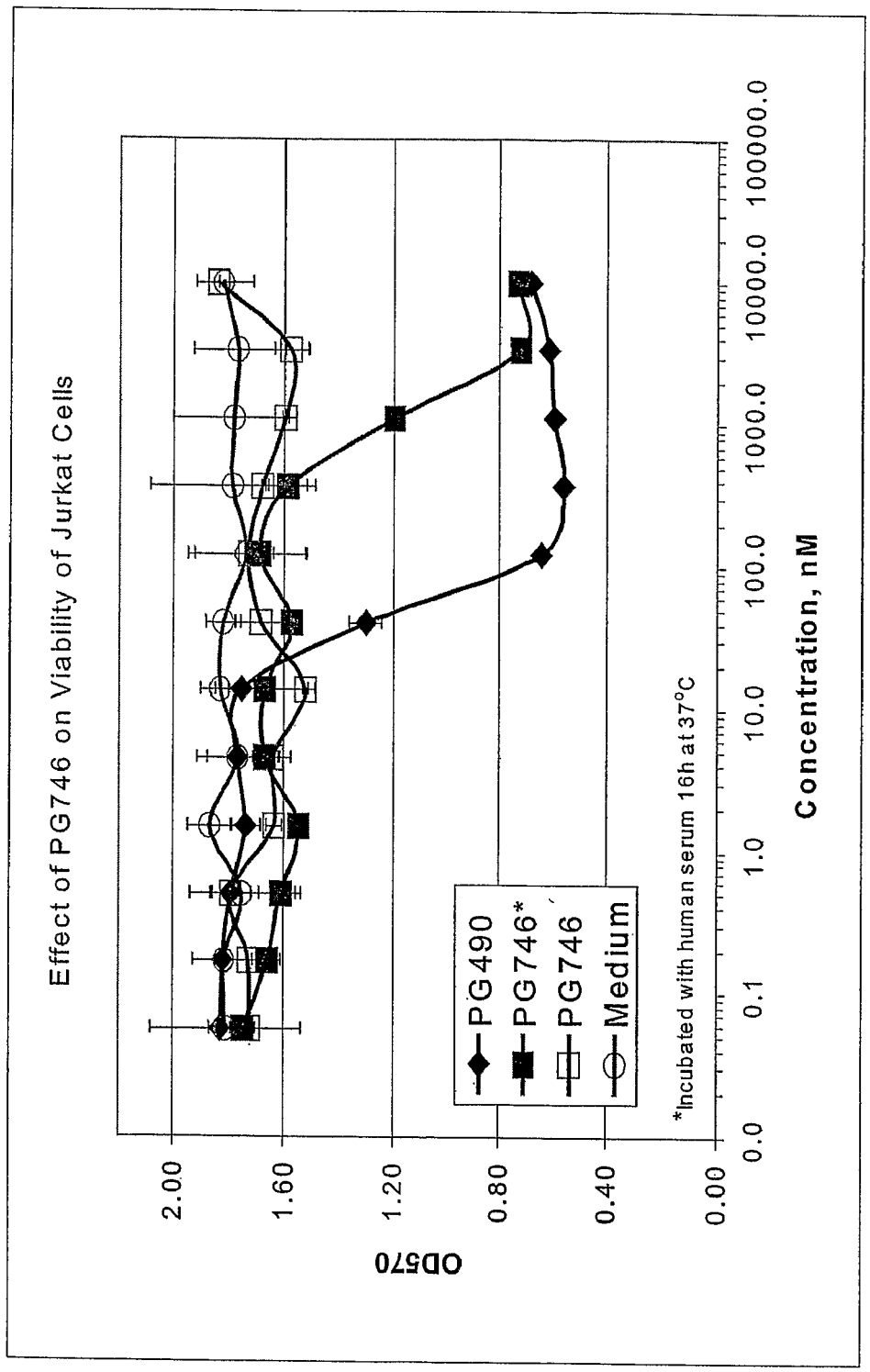
FIG. 2 shows the cytotoxic effect in Jurkat cells of a compound of the invention, 14-acetyl-5,6-didehydro triptolide (designated PG746), in comparison with triptolide (designated PG490) (Example 9)

The terms below have the following meanings unless indicated otherwise.

"Alkyl" refers to a fully saturated acyclic moiety consisting of carbon and hydrogen, which may be linear or branched. Examples of alkyl groups are methyl, ethyl, n-butyl, t-butyl, n-heptyl, and isopropyl. Generally preferred are lower alkyl groups, having one to six carbon atoms, as exemplified by methyl, ethyl, n-butyl, i-butyl, t-butyl, isoamyl, n-pentyl, and isopentyl. In other embodiments, lower alkyl includes groups having one to four carbon atoms, or 1-2 carbon atoms (methyl and ethyl).

"Cycloalkyl" refers to a fully saturated cyclic moiety consisting of carbon and hydrogen, having three to eight carbon atoms, preferably three to six carbons atoms; e.g. cyclopropyl or methylcyclopentyl. "Cycloalkenyl" refers to an unsaturated cyclic moiety consisting of carbon and hydrogen, having five to eight carbon atoms, preferably five or six carbon atoms.

"Alkenyl" refers to an unsaturated acyclic moiety consisting of carbon and hydrogen, which may be linear or branched, having one or more double bonds. Generally preferred are lower alkenyl groups, having two to six, or two to four, carbon atoms. "Alkynyl" refers to an unsaturated acyclic moiety consisting of carbon and hydrogen, which may be linear or branched, containing one or more triple bonds. Generally preferred are lower alkynyl groups, having two to six, or two to four, carbon atoms.

"Aryl" refers to a substituted or unsubstituted monovalent aromatic radical, generally having a single ring (e.g., benzene) or two condensed rings (e.g., naphthyl), where monocyclic aryl groups are preferred. The term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group, preferably one or two ring hydrogens, is replaced with a group preferably selected from fluorine, chlorine, bromine, methyl, ethyl, hydroxy, hydroxymethyl, nitro, amino, methylamino, dimethylamino, methoxy, halomethoxy, and halomethyl.

"Acyloxyalkyl" refers to a substituent of the form —R—O—(C=O)—R', where R is alkyl, preferably having up to six carbon atoms, and R' is selected from alkyl, alkenyl, alkynyl, aryl, and aralkyl, where R' preferably comprises lower alkyl, lower alkenyl, or lower alkynyl (i.e. $C_2$-$C_6$) groups and monocyclic aryl groups.

"Aralkyl" refers to an alkyl, preferably lower ($C_1$-$C_4$, more preferably $C_1$-$C_2$) alkyl, substituent which is further substituted with an aryl group, preferably a monocyclic aryl group; examples are benzyl and phenethyl. Also included is fluorenylmethyl, a component of the widely employed Fmoc (fluorenylmethoxycarbonyl) protecting group.

A "5- to 7-member heterocyclic ring whose ring atoms are selected from the group consisting of carbon, nitrogen, oxygen and sulfur, wherein the ring atoms include at most 3 heteroatoms" preferably refers to a non-aromatic ring, and includes such nitrogen heterocycles as pyrrolidine, piperidine, and morpholine.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethyl ammonium, bis(2-hydroxyethyl) ammonium, phenylethylbenzylammonium, dibenzylethylene diammonium, and the like. Other cations encompassed by the above term include the protonated form of procaine, quinine and N-methylglucosanine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

II. Triptolide 5,6-Derivatives

A. Compounds and Preferred Embodiments

For the purposes of the current disclosure, the following numbering scheme is used for triptolide and triptolide derivatives:

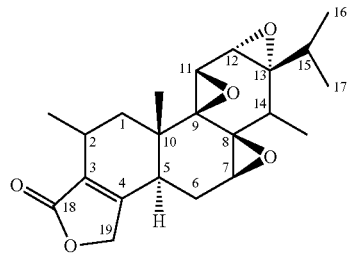

The compounds of the invention are derivatives of triptolide resulting from modification at the 5 and/or 6 position.

In one embodiment, the compound is 5α-hydroxytriptolide, which may be prepared as described below. This compound may be used as an entry point for preparation of other compounds modified at the 5 and/or 6 position.

In addition, the hydroxyl groups of the starting material, e.g. triptolide, tripdiolide (2-hydroxytriptolide) or 16-hydroxytriptolide, may be derivatized as esters or carbonates.

The compounds are represented by Formulas I and II below:

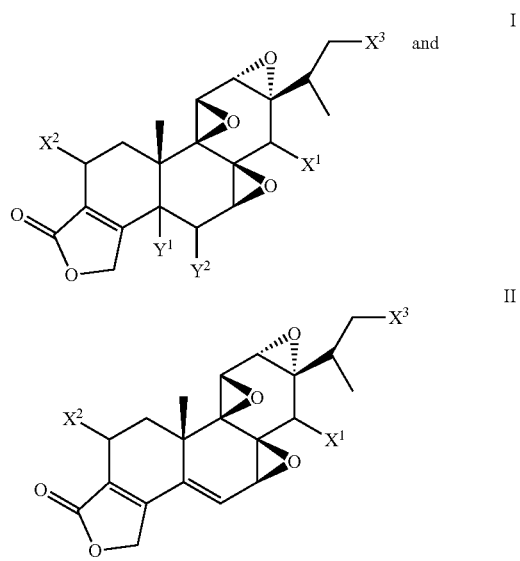

where $X^1$ is $OR^1$, where $R^1$ is selected from hydrogen, $C(=O)R^2$, and $C(=O)OR^2$, where $R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;

$X^2$ and $X^3$ are independently $OR^1$ or hydrogen, at least one of $x^2$ and $X^3$ being hydrogen.

In formula I, $Y^1$ and $Y^2$ are defined according to one of the following three embodiments:

(i) $Y^1$ is hydrogen and $Y^2$ is selected from the group consisting of hydroxyl, halogen, cyano, nitromethyl, ethenyl, —$CH_2COOR^4$, $N(R^4)_2$, and $SR^4$. Preferred embodiments of this class include those in which $Y^2$ is hydroxyl, fluoro, chloro, bromo, cyano, —$CH_2COOR^4$, or $N(R^4)_2$. In further preferred embodiments, $Y^2$ is hydroxyl, fluoro, chloro, bromo, or cyano. In one preferred embodiment, $Y^2$ is hydroxyl; in another preferred embodiment, $Y^2$ is cyano.

(ii) $Y^1$ is hydroxyl and $Y^2$ is selected from the group consisting of hydrogen, hydroxyl, halogen, cyano, $N(R^4)_2$, and $SR^4$. Preferred embodiments of this class include those in which $Y^2$ is hydrogen, hydroxyl, fluoro, chloro, bromo, or cyano. In one embodiment, $Y^2$ is hydrogen; in a further embodiment, $Y^2$ is hydroxyl.

(iii) $Y^1$ and $Y^2$ taken together form an epoxide ring.

Each group $R^4$ is independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl, or, in the case of $N(R^4)_2$, taken together form a 5- to 7-member heterocyclic ring whose ring atoms are selected from the group consisting of carbon, nitrogen, oxygen and sulfur, where the ring atoms include at most 3 heteroatoms.

Preferably, $X^1$ is selected from OH and $OC(=O)R^2$ (that is, $R^1$ is selected from hydrogen and $C(=O)R^2$). When $R^1$ is $C(=O)R^2$, $R^2$ is preferably selected from alkyl, aryl, aralkyl, and alkoxyalkyl, and is more preferably selected from alkyl, e.g. methyl or ethyl; aryl, e.g. phenyl, and aralkyl, e.g. benzyl. In one embodiment, $R^2$ is methyl.

When either of $X^2$ and $X^3$ is $OR^1$, preferred embodiments of $R^1$ are as described above.

In one embodiment, each of $X^2$ and $X^3$ is hydrogen.

The groups defined above as $R^2$, $R^3$, and $R^4$, when selected from alkyl, alkenyl, and alkynyl, preferably have up to six carbon atoms, more preferably up to four carbons, and, in selected embodiments, one or two carbons. When selected from cycloalkyl or cycloalkenyl, they preferably have 3 to 7, or, for cycloalkenyl, 5 to 7 carbon atoms. When selected from aralkyl, hydroxyalkyl, alkoxyalkyl, aryloxyalkyl, and acyloxyalkyl, the alkyl components of these groups preferably have up to six carbon atoms, more preferably up to four carbons, and, in selected embodiments, one or two carbons. In further selected embodiments, each of these groups is independently selected from alkyl, aryl, aralkyl, and alkoxyalkyl.

B. Preparation of Invention Compounds

The compounds of the invention may be prepared from triptolide, tripdiolide (2-hydroxy triptolide) or 16-hydroxytriptolide. Triptolide can be obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for preparing triptolide, tripdiolide and 16-hydroxytriptolide are known in the art and are described, for example, in Kupchan et al. (1972, 1977); Lipsky et al. (1994); Pu et al. (1990); and Ma et al. (1992).

Compounds of formula I above in which $Y^1$=OH and $Y^2$=H, e.g. 5α-hydroxy triptolide (designated herein as PG701), may be prepared by reaction of the starting triptolide compound with selenium dioxide, as illustrated in Example 1 below. Such compounds may then be used for preparation of compounds of formula II by dehydration. This is illustrated in Examples 2-3 below, where the free 14-hydroxyl group is first derivatized as acetyl, and (diethylamino)sulfur trifluoride (DAST) is used for dehydration.

The 5,6-olefin of formula II can then be used to prepare further compounds of formula I in which (i) $Y^1$ is hydrogen and $Y^2$ is selected from the group consisting of hydroxyl, halogen, cyano, nitromethyl, ethenyl, —$CH_2COOR^4$, $N(R^4)_2$, and $SR^4$, where each $R^4$ is independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl, or, in the case of $N(R^4)_2$, taken together form a 5- to 7-member heterocyclic ring whose ring atoms are selected from the group consisting of carbon, nitrogen, oxygen and sulfur, wherein the ring atoms include at most 3 heteroatoms; or (ii) $Y^1$ is hydroxyl and $Y^2$ is selected from the group consisting of hydrogen, hydroxyl, halogen, cyano, $N(R^4)_2$, and $SR^4$; or (iii) $Y^1$ and $Y^2$ taken together form an epoxide ring.

For example, compounds of formula I in which $Y^1$ is hydrogen and $Y^2$ is hydroxyl can be prepared by hydration of the 5,6-olefin of formula II, according to known procedures, e.g. as illustrated in Example 4 below. Compounds of formula I in which $Y^1$ is hydrogen and $Y^2$ is a halogen can be prepared by reaction of the hydroxylated compound with a halogenation reagent, e.g. $CBr_4$ for production of the bromide. Alternatively, the 5,6-olefin may be reacted with a hydrohalic acid HX or its synthetic equivalent, in accordance with know procedures.

Compounds of formula I in which $Y^1$ is hydrogen and $Y^2$ is selected from the group consisting of cyano, nitromethyl, ethenyl, —$CH_2COOR^4$, $N(R^4)_2$, and $SR^4$ can be formed by Michael addition of a nucleophilic species to the conjugated olefin of formula II, as illustrated in Example 7 for addition of a cyano group.

Compounds of formula I in which $Y^1$ and $Y^2$ taken together form an epoxide ring can be prepared by epoxidation of the 5,6-olefin of formula II, according to known procedures, e.g. using MCPBA, as illustrated in Example 5 below. Ring-opening of the epoxide can be then be used to prepare compounds of formula I in which $Y^1$ is hydroxyl and $Y^2$ is selected from the group consisting of hydroxyl, halogen, cyano, $N(R^4)_2$, and $SR^4$, as defined above. Alternatively, compounds of formula I in which both $Y^1$ and $Y^2$ are hydroxyl can be prepared by direct hydroxylation of the 5,6-olefin of formula II, e.g. oxidation with periodate, as illustrated in Example 6 below.

Examples of the synthetic transformations described above are depicted in Schemes 1 and 2 below. Of course, these synthetic conversions are not limited to the use of the reagents shown, and various other reagents may be used to effect these conversions, as known and available to those skilled in the art. In addition, any free hydroxyl groups on the starting triptolide compounds may be protected as desired.

The relative stereochemistry of substituents at the 5 and/or 6 positions in the compounds of formula I will be determined by steric constraints, and are shown in Schemes 1 and 2 for the reactions depicted therein.

Scheme 1

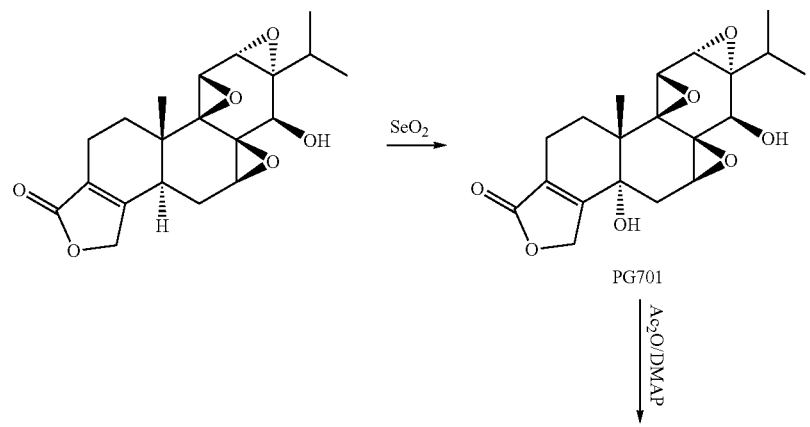

PG701

Ac$_2$O/DMAP

-continued
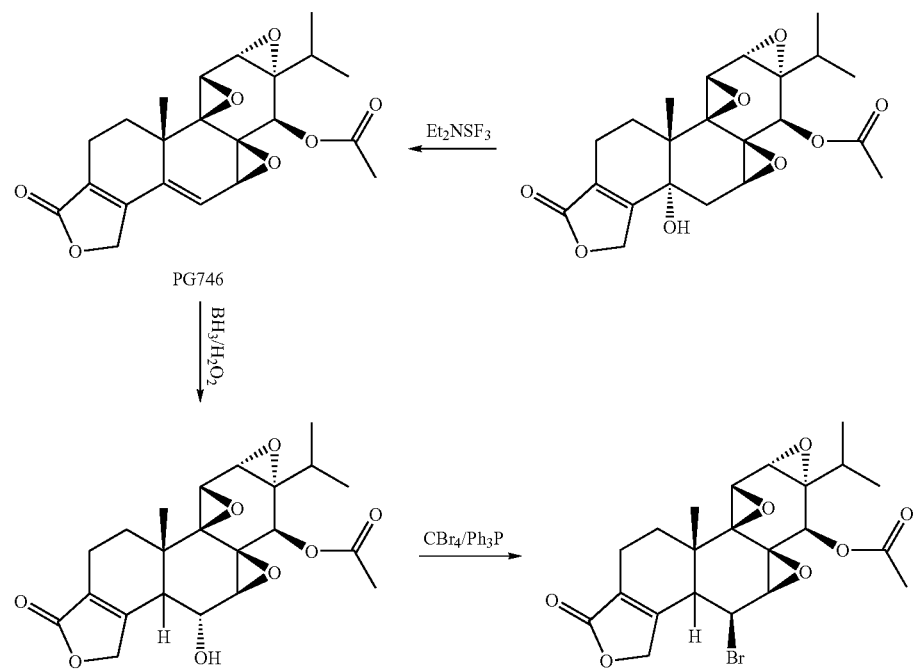
Scheme 2
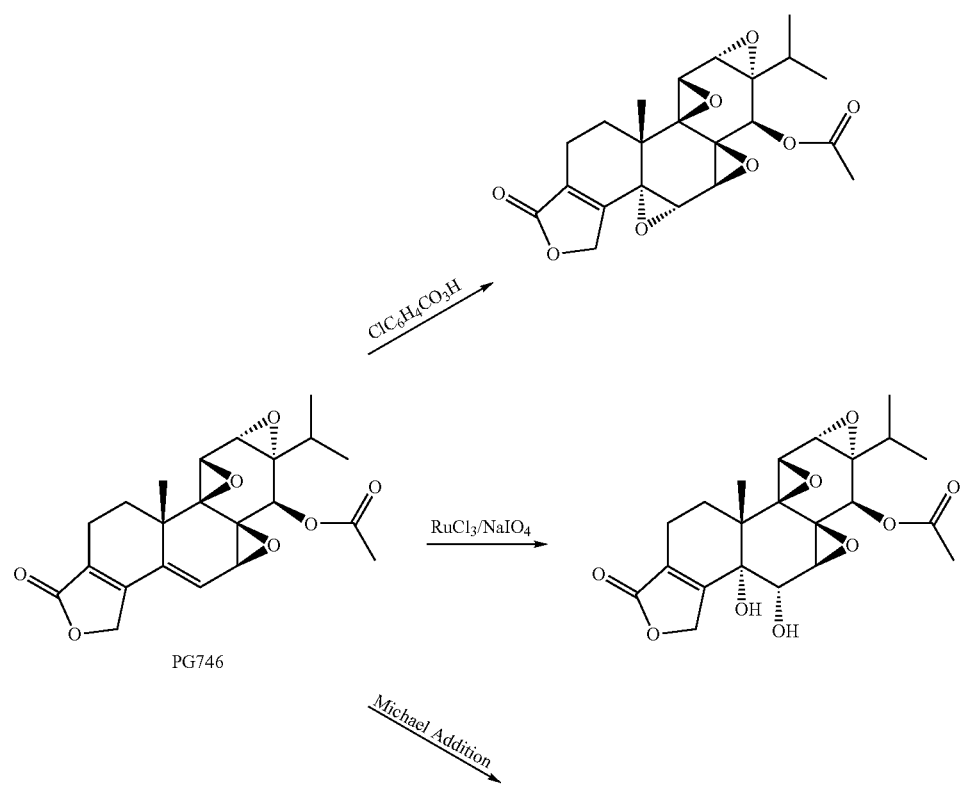

-continued

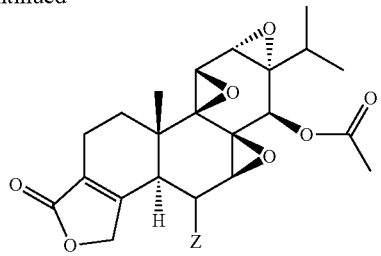

III. Therapeutic Compositions

Formulations containing the compounds of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide derivative in a suitable intravenous solution, such as sterile physiological salt solution.

Liquid compositions can be prepared by dissolving or dispersing the invention compounds (generally about 0.5% to about 20% by weight) and optional pharmaceutical adjuvants in a pharmaceutically acceptable carrier, such as, for example, aqueous saline, aqueous dextrose, glycerol, or ethanol, to form a solution or suspension.

The compounds may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see REMINGTON'S PHARMACEUTICAL SCIENCES (19th Ed., Williams & Wilkins, 1995). The composition to be administered will contain a quantity of the selected compound in an effective amount for effecting immunosuppression in a subject or apoptosis in a targeted cell.

IV. Immunomodulating and Antiinflammatory Treatment

Figure 3:
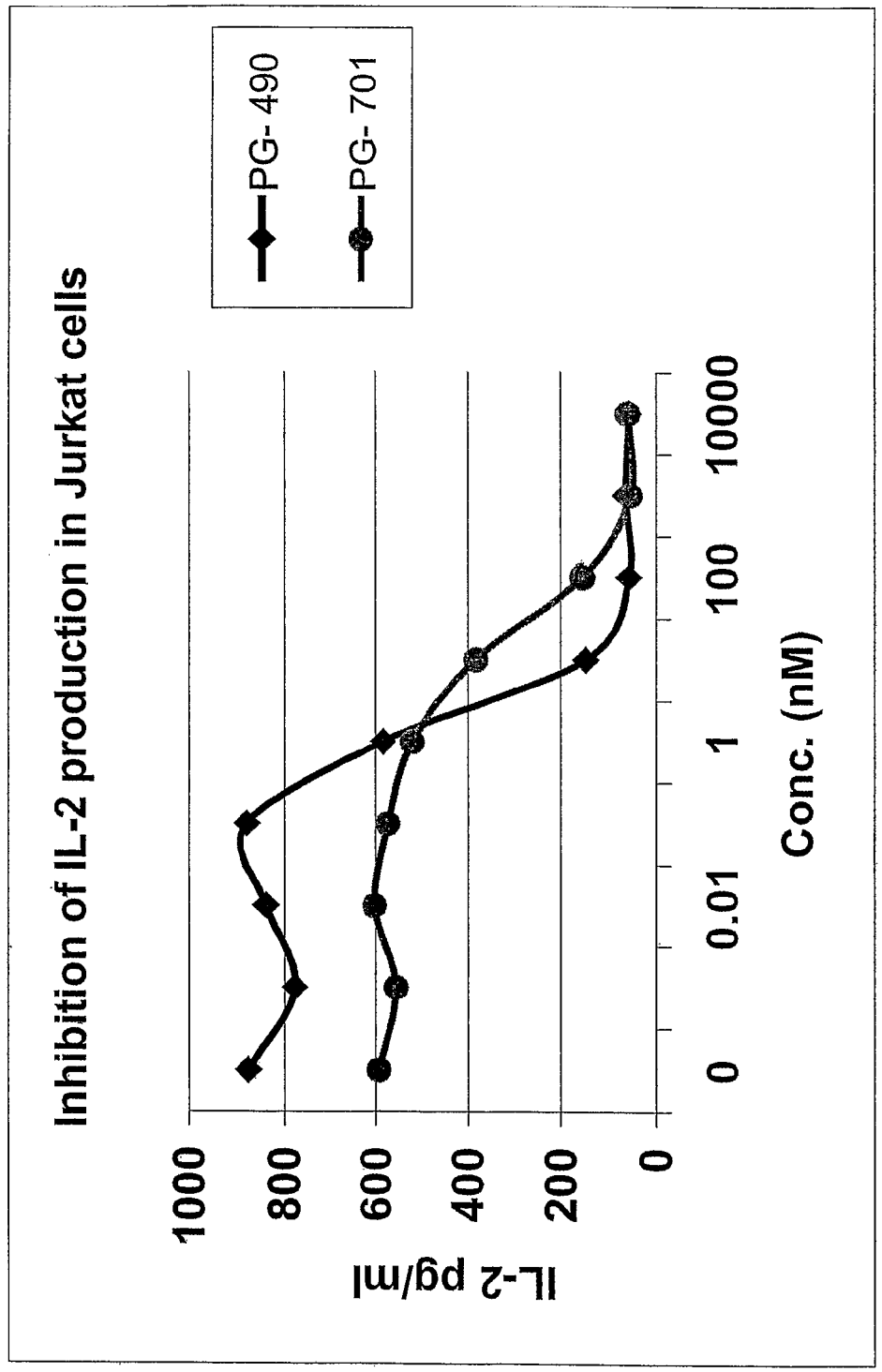
FIGS. 3 and 4 show inhibition of IL-2 production in Jurkat cells by invention compounds PG701 and PG746, respectively, in comparison with triptolide (PG490) (Example 10).

The compounds of the present invention are shown to have immunosuppressive activity. As shown in FIG. 3, a compound of formula I, 5α-hydroxy triptolide (designated PG701) inhibited IL-2 production in Jurkat cells (see Example 10) in a dose-dependent manner, at concentrations of about 10 nM or greater. A compound of formula II, 14-acetyl-5,6-didehydro triptolide (designated PG746) acts as a prodrug under physiological conditions. In assay medium, the compound showed no significant activity relative to the medium control. However, after incubation for 16 hours with human serum, the compound inhibited IL-2 production in Jurkat cells in a dose-dependent manner, at concentrations of about 10 nM or greater.

The invention thus includes the use of the invention compounds as immunosuppressive agents, e.g. as an adjunct to transplant procedures or in treatment of autoimmune disease.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-mallow transplant or other transplant of hematopoietic stem cells from a donor tissue source containing mature lymphocytes, the transferred lymphocytes recognize the host tissue antigens as foreign. These cells become activated and mount an attack upon the host (a graft-versus-host response) that can be life-threatening. Moreover, following an organ transplant, the host lymphocytes recognize the foreign tissue antigens of the organ graft and mount cellular and antibody-mediated immune responses (a host-versus-graft response) that lead to graft damage and rejection.

One result of an autoimmune or a rejection reaction is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off.

Indeed, patients treated with such nonspecific immunosuppressive agents are as likely to succumb from infection as they are from their autoimmune disease.

The compositions of the present invention are useful in applications for which triptolide and its prodrugs and other derivatives have proven effective, e.g. in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. Triptolide and the present derivatives are also useful for treatment of other inflammatory conditions, such as traumatic inflammation, and in reducing male fertility.

The compositions are useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The compositions are also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Hashimoto's thyroiditis, allergic encephalomyelitis, glomerulonephritis, and various allergies.

Further uses may include the treatment and prophylaxis of inflammatory and hyperproliferative skin diseases and cutaneous manifestations of immunologically mediated illnesses, such as psoriasis, atopic dermatitis, pemphigus, urticaria, cutaneous eosinophilias, acne, and alopecia areata; various eye diseases such as conjunctivitis, uveitis, keratitis, and sarcoidosis; inflammation of mucous and blood vessels such as gastric ulcers, vascular damage caused by ischemic diseases and thrombosis, ischemic bowel diseases, inflammatory bowel diseases, and necrotizing enterocolitis; intestinal inflammations/allergies such as Coeliac diseases and ulcerative colitis; renal diseases such as interstitial nephritis, Good-pasture's syndrome, hemolytic-uremic syndrome and diabetic nephropathy; hematopoietic diseases such as idiopathic thrombocytopenia purpura and autoimmune hemolytic anemia; skin diseases such as dermatomyositis and cutaneous T cell lymphoma; circulatory diseases such as arteriosclerosis and atherosclerosis; renal diseases such as ischemic acute renal insufficiency and chronic renal insufficiency; and Behcet's disease.

The compositions and method of the invention are also useful for the treatment of inflammatory conditions such as asthma, both intrinsic and extrinsic manifestations, for example, bronchial asthma, allergic asthma, intrinsic asthma, extrinsic asthma and dust asthma, particularly chronic or inveterate asthma (for example, late asthma and airway hyperresponsiveness). The composition and method may also be used for treatment of other inflammatory conditions, including traumatic inflammation, inflammation in Lyme disease, chronic bronchitis (chronic infective lung disease), chronic sinusitis, sepsis associated acute respiratory distress syndrome, and pulmonary sarcoidosis. For treatment of respiratory conditions such as asthma, the composition is preferably administered via inhalation, but any conventional route of administration may be useful.

In treating an autoimmune condition, the patient is given the composition on a periodic basis, e.g., 1-2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient. The dose that is administered is preferably in the range of 1-25 mg/kg patient body weight per day, with lower amounts being preferred for parenteral administration, and higher amounts being preferred for oral administration. Optimum dosages can be determined by routine experimentation according to methods known in the art.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1-25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

In treatment or prevention of graft-versus-host disease, resulting from transplantation into a recipient of matched or mismatched bone marrow, spleen cells, fetal tissue, cord blood, or mobilized or otherwise harvested stem cells, the dose is preferably in the range 0.25-2 mg/kg body weight/day, preferably 0.5-1 mg/kg/day, given orally or parenterally.

Also within the scope of the invention is a combination therapy comprising a compound of formula I or II and one or more conventional immunosuppressive agents. These immunosuppressant agents within the scope of this invention include, but are not limited to, IMUREK™ (azathioprine sodium), brequinar sodium, SPANIDIN™ (gusperimus trihydrochloride, also known as deoxyspergualin), mizoribine (also known as bredinin), CELLCEPT™ (mycophenolate mofetil), NEORAL™ (Cyclosporin A; also marketed as a different formulation under the trademark SANDIMMUNE™), PROGRAF™ (tacrolimus, also known as FK-506), RAPIMMUNE™ (sirolimus, also known as rapamycin), leflunomide (also known as HWA-486), ZENA- PAX™, glucocortcoids, such as prednisolone and its derivatives, antibodies such as orthoclone (OKT3), and antithymyocyte globulins, such as thymoglobulins. The compounds are useful as potentiators when administered concurrently with another immunosuppressive drug for immunosuppressive treatments as discussed above. A conventional immunosuppressant drug, such as those above, may thus be administered in an amount substantially less (e.g. 20% to 50% of the standard dose) than when the compound is administered alone. Alternatively, the invention compound and immunosuppressive drug are administered in amounts such that the resultant immunosuppression is greater than what would be expected or obtained from the sum of the effects obtained with the drug and invention compound used alone. Typically, the immunosuppressive drug and potentiator are administered at regular intervals over a time period of at least 2 weeks.

The compositions of the invention may also be administered in combination with a conventional anti-inflammatory drug (or drugs), where the drug or amount of drug administered is, by itself, ineffective to induce the appropriate suppression or inhibition of inflammation.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichnann, 1984). Single cell suspensions are prepared from individual spleens, and microwell cultures are established in the presence and absence of concanavalin A to assess the extent of mitogenic responsiveness.

V. Anticancer Treatment

The compounds of the present invention are shown to have cytotoxic activity. As shown in FIG. 1, a compound of formula I, 5α-hydroxy triptolide (designated PG701) induced apoptosis in Jurkat cells (see Example 8) in a dose-dependent manner. A compound of formula II, 14-acetyl-5,6-didehydro triptolide (designated PG746) acts as a prodrug under physiological conditions. In assay medium (see Example 9), the compound showed no significant activity relative to the medium control. However, after incubation for 16 hours with human serum, the compound was clearly cytotoxic to Jurkat cells in this assay at concentrations of about 1 μM or greater.

The invention thus includes the use of the invention compounds as cytotoxic agents, particularly to treat cancers. As used herein, "cancer" refers to all types of cancer or neoplasm or malignant tumors found in mammals especially humans, including leukemias, sarcomas, carcinomas and melanoma.

The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs. The term "carcinoma" refers to a malignant new growth made up of epithelial cells tending to infiltrate the surrounding tissues and give rise to metastases.

Included, for example, are cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin, including malignant melanoma, and gastrointestinal tract), solid organs, the nervous system, e.g. glioma (see Y. X. Zhou et al., 2002), and musculo-skeletal tissue. The compounds may be used for treatment of various cancer cell types, including, but not limited to, brain, including medulloblastoma, head and neck, breast, colon, small cell lung, large cell lung, thyroid, testicle, bladder, prostate, liver, kidney, pancreatic, esophogeal, stomach, ovarian, cervical or lymphoma tumors. Treatment of breast, colon, lung, and prostate tumors is particularly contemplated.

The compositions may be administered to a patient afflicted with cancer and/or leukemia by any conventional route of administration, as discussed above. The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

Antitumor activity in vivo of a particular composition can be evaluated by the use of established animal models, as described, for example, in Fidler et al., U.S. Pat. No. 6,620, 843. Clinical doses and regimens are determined in accordance with methods known to clinicians, based on factors such as severity of disease and overall condition of the patient.

VI. Other Indications

The compounds of the present invention may also be used in the treatment of certain CNS diseases. Glutamate fulfills numerous physiological functions, including an important role in the pathophysiology of various neurological and psychiatric diseases. Glutamate excitotoxicity and neurotoxicity have been implicated in hypoxia, ischemia and trauma, as well as in chronic neurodegenerative or neurometabolic diseases, Alzheimer's dementia, Huntington's disease and Parkinson's disease. In view of the reported neuroprotective effects of triptolide, particularly protection from glutamate-induced cell death (Q. He et al., 2003; X. Wang et al., 2003), compounds of the invention are envisioned to antagonize the neurotoxic action of glutamates and thus may be a novel therapy for such diseases.

Recent evidence from MS patients in relapse suggests an altered glutamate homeostasis in the brain. Neurotoxic events occurring in MS patients can be responsible for oligodendrocyte and neuronal cell death. Antagonizing glutamate receptor-mediated excitotoxicity by treatment with compounds of this invention may have therapeutic implications in MS patients. Other CNS diseases such as Guillain-Barre syndrome, Meniere's disease, polyneuritis, multiple neuritis, mononeuritis and radiculopathy may also be treated with the compounds of the present invention.

The compounds of the present invention may also be used in the treatment of certain lung diseases. Idiopathic pulmonary fibrosis (PF) is a progressive interstitial lung disease with no known etiology. PF is characterized by excessive deposition of intracellular matrix and collagen in the lung interstitium and gradual replacement of the alveoli by scar tissue as a result of inflammation and fibrosis. As the disease progresses, the increase in scar tissue interferes with the ability to transfer oxygen from the lungs to the bloodstream. A 14-succinimide ester of triptolide has been reported to block bleomycin-induced PF (G. Krishna et al., 2001). Accordingly, the compounds of the present invention may be useful for treatment of PF. Treatment of other respiratory diseases, such as sarcoidosis, fibroid lung, and idiopathic interstitial pneumonia is also considered. Other diseases involving the lung and envisioned to be treatable by compounds of this invention include Severe Acute Respiratory Syndrome (SARS) and acute respiratory distress syndrome (ARDS). In particular, with respect to SARS, the reduction of virus content (SARS-CoV) before the peak of the disease process and the usefulness of corticosteroid treatment, as noted below, suggest that the development of the most severe, life-threatening effects of SARS may result from the exaggerated response of the body to the infection (immune hyperactivity) rather than effects of the virus itself. (See also copending and co-owned U.S. provisional application Ser. No. 60/483,335, which is incorporated herein by reference.) Corticosteroid treatment has been used in SARS patients to suppress the massive release of cytokines that may characterize the immune hyperactive phase, in the hope that it will stop the progression of pulmonary disease in the next phase. Corticosteroid treatment has produced good clinical results in reduction of some of the major symptoms of SARS. However, there are several treatment-related side effects, and there is a clear need for more selective immunosuppressive and/or anti-inflammatory agents.

EXAMPLES

The following examples illustrate but are not intended in any way to limit the invention.

Example 1

Synthesis of 5-α-hydroxytriptolide (PG701)

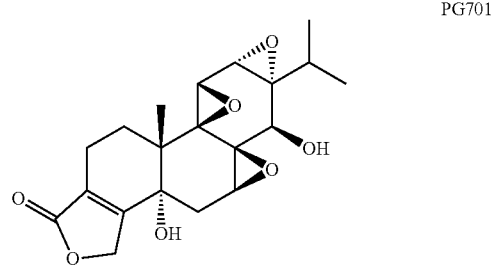

PG701

To a solution of triptolide (437.6 mg, 1.21 mmol) in 1,4-dioxane (35 mL) was added selenium dioxide (305.1 mg, 2.75 mmol). The reaction mixture was stirred at 90° C. under $N_2$ for 70 hrs. After cooling to room temperature, the reaction mixture was filtered through Celite and concentrated under vacuum. The crude product was purified via preparative TLC (ethyl acetate/dichloromethane 3:7) to yield the desired product (211.7 mg, 46.3%).

Analytical TLC: Rf=0.30 (ethyl acetate/hexanes/methanol 1:1:0.1).

IR (KBr): 3469.5, 2962.6, 2886.5, 1763.3, 1736.3, 1676.9, 1459.5, 1432.4, 1383.1, 1365.1, 1349.3, 1301.6, 1277.0, 1269.4, 1246.5, 1203.2, 1160.4, 1112.9, 1079.7, 1030.9, 988.0, 951.1, 945.3, 943.9, 907.7, 877.2, 855.2, 841.2, 812.7, 797.8, 780.4, 748.2, 656.1, 645.0, 605.5, 580.4, 555.7, 524.3, 498.7, 483.9, 469.5, 439.4, 428.9, 414.9, 407.1 $cm^{-1}$.

$H^1$NMR (300 MHz, $CDCl_3$): δ=0.90 (d, 3H, 16-$CH_3$), 1.02 (d, 3H, 17-$CH_3$) 1.18 (s, 3H, 20-$CH_3$), 1.28 (m, 1H, 1-CHb), 1.77 (m, 1H, 1-CHa), 2.08-2.42 (m, 5H, 2-$CH_2$, 6-$CH_2$ and 15-CH), 2.81 (t, 2H, 5-OH and 14-OH), 3.37 (d, 1H, 7-CH), 3.48 (d, 1H, 14-CH), 3.63 (d, 1H, 12-CH), 3.96 (d, 1H, 11-CH), 4.82 (m, 2H, 19-$CH_2$) ppm.

Example 2

Synthesis of 14-acetyl-5-α-hydroxytriptolide

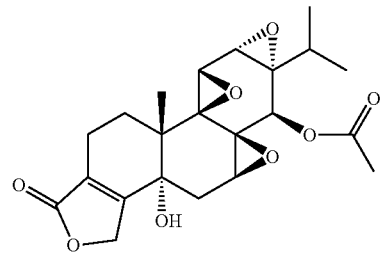

To a solution of 5-α-hydroxytriptolide (PG701, 98.3 mg, 0.261 mmol), 4-dimethylaminopyridine (DMAP, 45.2 mg) and triethylamine (TEA, 0.50 mL) in dichloromethane (5.0 mL) was added acetic anhydride (0.247 mL, 2.61 mmol, 10.0 eq) at room temperature under nitrogen. After stirring for 4-5 hrs at room temperature, methanol (1.0 mL) was added, and the reaction mixture was concentrated under vacuum. The crude product was purified using preparative TLC (ethyl acetate/hexanes/methanol 1.0: 1.0:0.1) to yield the desired product (95.7 mg, 87.6%).

Analytical TLC: Rf=0.43 (ethyl acetate/hexanes/methanol 1:1:0.1).

IR(KBr): 3491.2, 2970.1, 1752.5, 1685.8, 1676.8, 1474.3, 1459.2, 1439.1, 1375.0, 1230.4, 1154.7, 1033.3, 994.0, 951.2, 923.6, 899.9, 870.1, 777.3, 750.0, 646.0, 618.7, 605.4, 570.3, 547.3, 529.2, 506.8, 499.0, 491.9, 476.5, 463.3, 447.4, 431.4, 418.5, 401.2 cm$^{-1}$.

H$^1$NMR (300 MHz, CDCl$_3$): δ=0.86 (d, 3H, 16-CH$_3$), 0.97 (d, 3H, 17-CH$_3$), 1.12 (s, 3H, 20-CH$_3$), 1.30 (dd, 1H, 1-CHb), 1.74 (m, 1H, 1-CHa), 1.90 (m, 1H, 15-CH), 2.06-2.40 (m, 4H, 2-CH$_2$ and 6-CH$_2$), 2.80 (s, 1H, 5-OH), 3.46 (d, 1H, 7-CH), 3.62 (d, 1H, 12-CH), 3.86 (d, 1H, 11-CH), 4.82 (m, 2H, 19-CH$_2$), 5.14 (d, 1H, 14-CH) ppm.

Example 3

Synthesis of 14-acetyl-5,6-didehydrotriptolide (PG746)

PG746

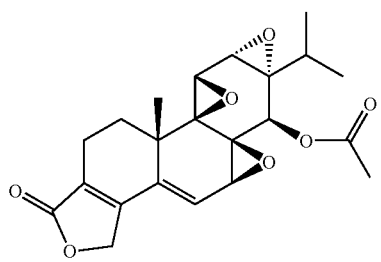

To a solution of 14-acetyl-5-α-hydroxytriptolide, prepared as described in Example 2 (10.5 mg, 0.025 mmol), in dichloromethane (0.50 mL) at 0° C. was added (diethylamino)sulfur trifluoride (DAST, 4.3 μL, 0.033 mmol, 1.3 eq). The reaction mixture was stirred at 0° C. under N$_2$ for 40 mins. Saturated NaHCO$_3$ aqueous solution (0.2 mL) diluted with 0.3 mL H$_2$O was added to the reaction mixture at 0° C. The mixture was then extracted with dichloromethane (1.5, 2×2.0 mL). The combined organic layers were dried over anhydrous Na$_2$SO$_4$ and concentrated under vacuum. The crude product was purified using preparative TLC (ethyl acetate/hexanes/methanol 40:60:5.0) to yield the desired product (4.0 mg, 39.8%).

Analytical TLC: Rf=0.71 (ethyl acetate/hexanes/methanol 1:1:0.1).

IR (KBr): 2969.7, 2880.3, 1747.8, 1686.2, 1655.3, 1649.3, 1625.6, 1438.1, 1371.1, 1305.7, 1224.9, 1154.4, 1101.0, 1081.7, 1028.1, 995.0, 975.5, 952.5, 938.3, 921.1, 895.4, 870.5, 846.2, 821.1, 785.5, 747.1, 638.4, 614.4, 588.4, 560.4, 546.2, 523.2, 511.1, 498.7, 480.5, 430.1, 416.5 cm$^{-1}$.

H$^1$NMR (300 MHz, CDCl$_3$): δ=0.86 (d, 3H, 16-CH$_3$), 0.98 (d, 3H, 17-CH$_3$), 1.30 (s, 3H, 20-CH$_3$), 1.40 (m, 1H, 1-CHb), 1.49 (m, 1H, 1-CHa), 1.91 (m, 1H, 15-CH), 2.33 (m, 1H, 2-CHb), 2.46 (m, 1H, 2-CHa), 3.54 (m, 2H, 12-CH and 7-CH), 3.80 (d, 1H, 11-CH), 4.90 (m, 2H, 19-CH$_2$), 5.20 (s, 1H, 14-CH), 5.99 (d, 1H, 6-CH) ppm.

Example 4

Synthesis of 14-acetyl-6-α-hydroxytriptolide

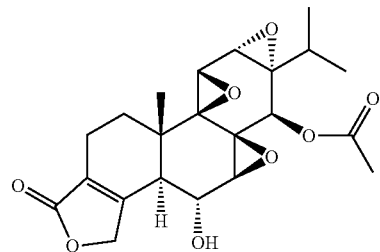

To a solution of 14-acetyl-5,6-didehydrotriptolide (PG746) (prepared as described in Example 3) in THF at room temperature under N$_2$ was added BH$_3$.THF (1.0M in THF). The reaction mixture was stirred at room temperature for 3 hrs, and NaOH (1.0N in H$_2$O) was then added, followed by the addition of H$_2$O$_2$ (50% by weight in H$_2$O). The mixture was extracted with dichloromethane for three times, and the combined organic layers were dried over anhydrous Na$_2$SO$_4$. After removal of solvent, the crude product was purified with preparative TLC.

Example 5

Synthesis of 14-acetyl-5,6-epoxytriptolide

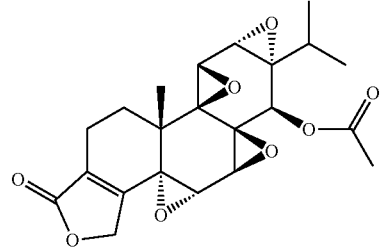

To a solution of 14-acetyl-5,6-didehydrotriptolide (PG746) in dichloromethane at room temperature is added m-chloroperbenzoic acid (MCPBA, 1.25 eq). The reaction mixture is stirred overnight at room temperature, filtered, washed with 10% NaHCO$_3$ solution, and dried over anhydrous Na$_2$SO$_4$. After removal of solvent, the crude product is purified using preparative TLC.

Example 6

Synthesis of 14-acetyl-5α,6α-dihydroxytriptolide

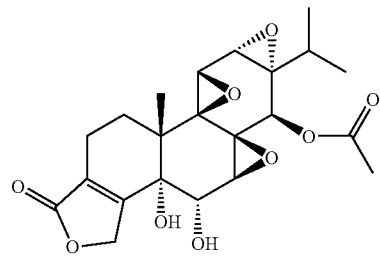

To a solution of 14-acetyl-5,6-didehydrotriptolide (PG746) in ethyl acetate/acetonitrile (1:1) at room temperature is added a solution of $RuCl_3.xH_2O$ and $NaIO_4$ in $H_2O$. A brown precipitate forms. The reaction mixture is stirred at room temperature for 15 mins and then poured into saturated aqueous $Na_2S_2O_3$. The mixture is extracted with dichloromethane three times, and the combined organic layers are dried over anhydrous $Na_2SO_4$. After removal of solvent, the crude product is purified using preparative TLC.

Example 7

Synthesis of 14-acetyl-6-cyanotriptolide

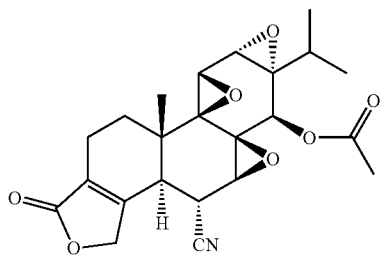

To a solution of 14-acetyl-5,6-didehydrotriptolide (PG746) in toluene at room temperature is added $Et_2AlCN$ (1.0M in toluene, 2.0 eq). The reaction mixture is stirred overnight at 45° C., cooled to room temperature, diluted with dichloromethane, washed with 10% $NaHCO_3$ solution, and dried over anhydrous $Na_2SO_4$. After removal of solvent, the crude product is purified using preparative TLC.

Example 8

Annexin V Apoptosis Assay

Test samples were diluted to 1 mM in complete tissue culture medium (RPMI 1640 medium plus 5% heat-inactivated fetal calf serum, 1% HEPES, 1% pen/strep, 1% glutamine). Aliquots were placed in microculture plates and serial dilutions were prepared so that the final concentration would encompass the range of 2 to 6,000 nM with half-log increments. Cells from an exponentially expanding culture of the Jurkat human T lymphoma cell line (#TIB-152 obtained from American Type Culture Collection, Manassas, Va.) were harvested, washed once by centrifugation, re-suspended in complete tissue culture medium, and further diluted to a concentration of $1\times10^6$ cells/ml. A volume of 100 μl of the cells ($1\times10^5$ cells) was added to wells containing 100 μl of the diluted compounds, and the plates were incubated at 37° C. in a 5% $CO_2$ incubator.

After 24 hours, the plates were centrifuged to pellet the cells, and the cells were washed twice with 2% heat-inactivated fetal calf serum in PBS. To each well, 500 ul of binding buffer was added, according to the Annexin V assay procedure (Bio Vision, Inc., Mountain View, Calif.). Next, 5 μl of the fluorescein isothiocyanate (FITC) conjugate of Annexin V (Bio Vision, Inc.) was added to each well, followed by 5 minutes of incubation in the dark. In some assays, propidium iodide (Bio Vision, Inc.) was added at this stage to check for necrotic cells. The contents of the wells were individually transferred into test tubes, and apoptosis was analyzed using a FACSCalibur flow cytometer (BD Immunocytometry Systems, San Jose, Calif.). Cells positive for Annexin V binding were considered to be apoptotic, and the data were calculated as percent apoptotic cells.

Data were plotted as the concentration of compound versus percent apoptotic cells. Data for invention compound 5α-hydroxy triptolide (designated PG701) and triptolide (designated PG490) are given in FIG. 1.

Example 9

Cytotoxicity (MTT) Assay

Test compounds were dissolved in DMSO at a concentration of 20 mM. Further dilutions were done in RPMI1640 medium (GIBCO, Rockville, Md.) supplemented with 10% Fetal Calf Serum (HyClone Laboratories, Logan, Utah). Invention compound 14-acetyl-5,6-didehydrotriptolide (designated PG746) was tested with and without a previous 16-hr incubation in human serum. Such incubation is expected to substantially convert the 14-acetyl group of PG746 to a 14-hydroxy group.

Cytotoxicity of the compounds was determined in a standard MTT assay using Cell Proliferation Kit I (#1 465 007, Roche Diagnostics, Mannheim, Germany). Accordingly, human T cell lymphoma (Jurkat) cells ($4\times10^5$ per well) were cultured for 24 h, in 96-well tissue culture plates, in the presence of serial three-fold dilutions of test compounds or medium containing the same concentration of DMSO as in the test samples at each dilution point. The cultures were then supplemented with 10 μl/well MTT reagent for 4 h and then with 0.1 ml/well solubilizing reagent for an additional 16 h. Optical density at 570 nm was measured on a ThermoScan microplate reader (Molecular Devices, Menlo Park, Calif.).

The data is presented as $OD_{570}$ values versus concentration of the compounds. The results for invention compound 14-acetyl-5,6-didehydrotriptolide (designated PG746) and triptolide (designated PG490) are given in FIG. 2.

Example 10

IL-2 Inhibition Assay

Test compounds were diluted to 1 mM in complete tissue culture medium. Aliquots were placed in microculture plates coated with anti-CD3 antibody (used to stimulate the production of IL-2 by Jurkat cells), and serial dilutions were prepared so that the final concentration would encompass the range of 0.001 to 10,000 nM in log increments.

Invention compound 14-acetyl-5,6-didehydrotriptolide (designated PG746) was tested with and without a previous 16-hr incubation in human serum. Such incubation is expected to substantially convert the 14-acetyl group of PG746 to a 14-hydroxy group.

Cells from an exponentially expanding culture of Jurkat human T cell line (#TIB-152 obtained from American Type Culture Collection, Manassas, Va.) were harvested, washed once by centrifugation, re-suspended in complete tissue culture medium, and diluted to a concentration of $10^7$ cells/ml. A volume of 50 μl of Jurkat cells was added to wells containing 100 μl of the diluted compounds, and the cells were stimulated with 50 ng/ml PMA and 10 mg/ml PHA. The plates were incubated at 37° C. in a 5% $CO_2$ incubator. After 24 hours, the plates were centrifuged to pellet the cells, 150 μl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as pg/ml of IL-2.

Figure 4:
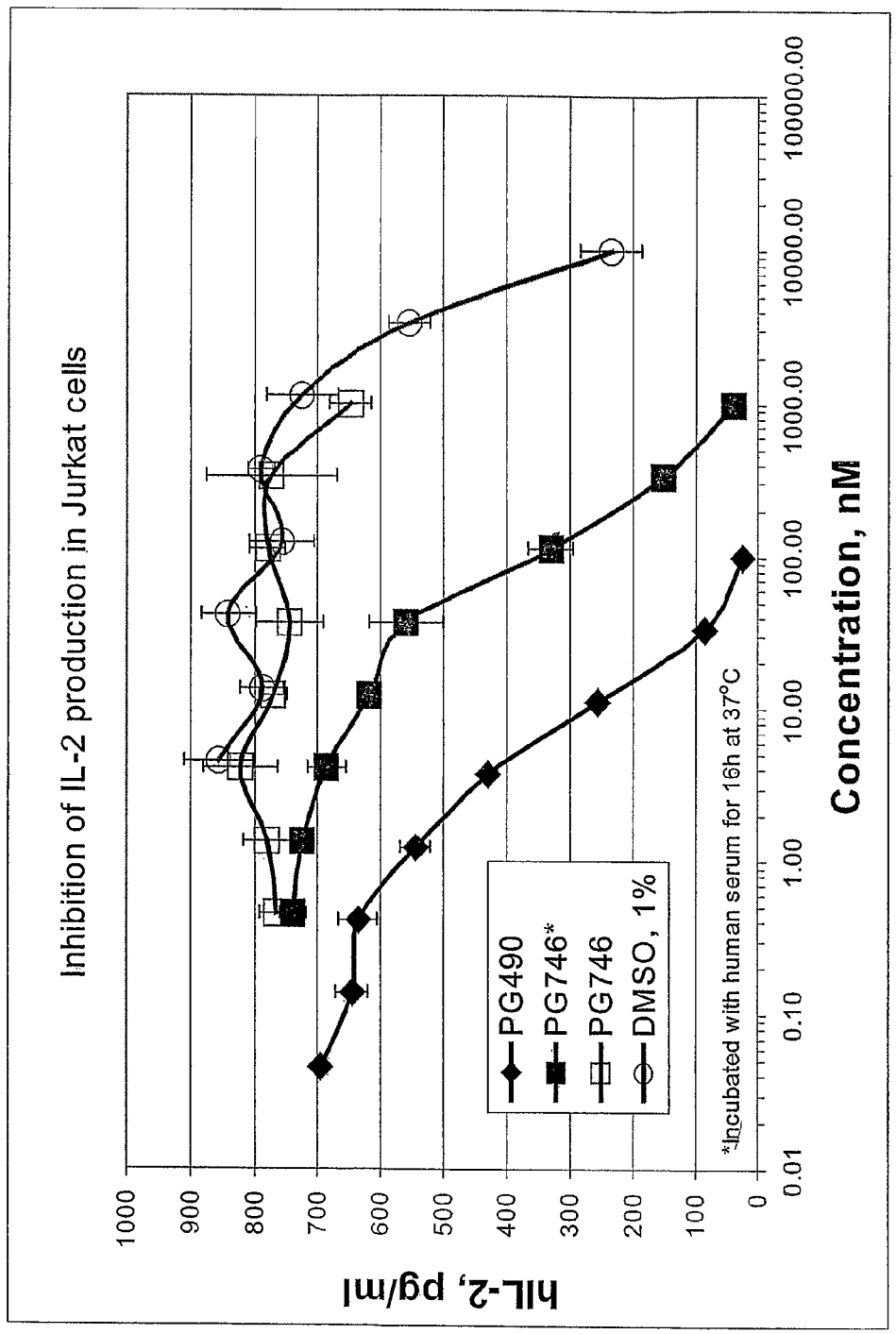

The data were plotted as the concentration of compound versus IL-2 concentration. The results for PG701 (5α-hydroxy triptolide), compared with PG490 (triptolide) and a solvent control, are given in FIG. 3. The results for PG746 (14-acetyl-5,6-didehydro triptolide), with and without incubation in human serum, compared with PG490 (triptolide) and a solvent control, are given in FIG. 4.

While the invention has been described with reference to specific methods and embodiments, it will be appreciated that various modifications may be made without departing from the invention.

It is claimed:

1. A compound having the structure I:

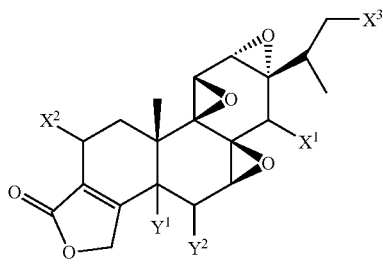

where $X^1$ is $OR^1$, where $R^1$ is selected from hydrogen, $C(=O)R^2$, and $C(=O)OR^2$, where $R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;

each of $X^2$ and $X^3$ is hydrogen;

and where $Y^1$ is hydrogen and $Y^2$ is cyano.

2. A method of preparing a 5-hydroxy triptolide compound of formula I:

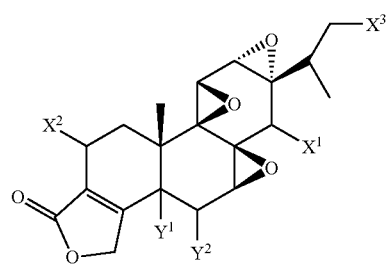

where $X^1$ is $OR^1$, where $R^1$ is selected from hydrogen, $C(=O)R^2$, and $C(=O)OR^2$, where $R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;

$X^2$ and $X^3$ are independently $OR^1$ or hydrogen, at least one of $X^2$ and $X^3$ being hydrogen;

$Y^1$=OH; and $Y^2$=H;

by reaction of a starting triptolide compound of formula I in which $X^1$, $X^2$ and $X^3$ are as defined above, $Y^1$=H, and $Y^2$=H, with selenium dioxide.

3. The method of claim 2, wherein $R^1$ is selected from hydrogen and $C(=O)R^2$, and $R^2$ is selected from lower alkyl, phenyl, and benzyl.

4. The method of claim 3, where $R^1$ is hydrogen.

5. The method of claim 4, wherein each of $X^2$ and $X^3$ is hydrogen, and said 5-hydroxy triptolide compound is 5α-hydroxytriptolide.

* * * * *